United States Patent [19]

Shoesmith

[11] Plant 5,088

[45] Aug. 16, 1983

[54] CHRYSANTHEMUM NAMED COPPER MINE

[75] Inventor: Leonard H. Shoesmith, Westfield-Woking, England

[73] Assignee: Pan American Plant Company, Parrish, Fla.

[21] Appl. No.: 359,748

[22] Filed: Mar. 19, 1982

[51] Int. Cl.[3] ..... A01H 5/00

[52] U.S. Cl. ..... Plt./79

[58] Field of Search ..... Plt./79

*Primary Examiner*—Robert E. Bagwill

*Attorney, Agent, or Firm*—Chas. W. Rummler

[57] ABSTRACT

A new variety of chrysanthemum plant of a semi-incurve standard type having large ball-shaped blooms of a golden bronze coloring, borne on long strong stems and which may be flowered year round in high light areas with a uniform eight-week response under high and low temperatures.

1 Drawing Figure

BACKGROUND OF THE NEW PLANT

This new chrysanthemum originated as a seedling of unknown parentage grown in greenhouse at West Chicago, Ill., from seeds of plants selected by me from a field of miscellaneous varieties randomly hybridized with the object of finding unusual plants having good growth habits and attractive color characteristics of commercial merit. This particular plant was selected for asexual propagation and test because of the very attractive golden bronze coloration of its large blooms, its vigorous and rapid growth habit, and its long strong stems resulting from careful disbudding. Propagation of this plant through successive generations, by means of vegetative cuttings, at West Chicago, Ill., has shown that its novel characteristics hold true and appear to be firmly fixed.

DESCRIPTION OF THE DRAWINGS

This new chrysanthemum cultivar is illustrated by the accompanying full color drawing, which shows a photographic rendition of blooms of this variety depicting their nature, form and coloration; the color of the florets of the blooms being shown as nearly true as it is reasonably possible to obtain through professional photographic procedures.

DESCRIPTION OF THE NEW PLANT

The following is a detailed description of this new variety of chrysanthemum plant with color descriptions according to The R.H.S. Colour Chart published by The Royal Horticultural Society of London, England.

THE PLANT

Origin: Seedling.
Parentage: Unknown.
Classification:
*Botanic.*—Hybrid *Chrysanthemum morifolium.*
*Commercial.*—Greenhouse standard cut flower.
Form: Semi-incurve standard.
Height: Tall; from 3 to 6 feet.
Growth: Vigorous, strong, sturdy and upright.
Growth rate: Rapid.
Branching character: Normal.
Foliage: Abundant in quantity.

*Leaf size.*—Up to about 12 cm. long and about 8 cm. wide.
*Shape of leaf.*—Ovate with cleft margins.
*Texture.*—Leathery.
*Color.*—Upper side — 147A. Under side — 147B.
*Ribs and veins.*—Pinnate.
*Petioles.*—Length — Up to about 30 mm.

THE BUD

Form: Globular.
Size: Varies in both diameter and length.
Rate of opening: Varies with temperature.
Color:
*When phyllaries first divide.*—22C.
*When petals begin to unfurl.*—22C.
Phyllaries:
*Number.*—About 45.
*Shape.*—Lanceolate.
*Color.*—147C.
Peduncle:
*Length.*—From 4 to about 7 cm.
*Aspect.*—Pubescent.
*Character.*—Rigid.
*Color.*—147C.

THE FLOWER

Blooming habit: Recurrent.
Blooming character: This plant may be flowered year round in high light areas with a uniform eight-week response under high and low temperatures.
Size of bloom: Very large.
*Diameter.*—About 11 to 14 cm.
Shape: A completely double composite inflorescence borne on a receptacle surrounded by an involucre of bracts. When the bloom first opens, it is cup-shaped and when the bloom matures it is flattened.
Borne: Singly when disbudded. Otherwise in raceme cluster.
Petalage:
*Number of ray florets.*—Many.
*Phyllaries.*—About 45.
*Arrangement.*—Imbricated.
*Form.*—Incurved with entire margins.
*Texture.*—Soft.
*Appearance.*—Satiny.
*Color of incurved florets.*—Inside — 22A. Outside — 22C.

Peduncle:

*Length.*—4 to 7 cm.

*Color.*—147C.

Persistence: The florets hang on and dry.

Fragrance: Typical chrysanthemum.

Lasting quality:

*On plant.*—3 to 4 weeks.

*As cut flower.*—2 to 3 weeks.

REPRODUCTIVE ORGANS

Stamens: 5 in number and in syngenesious arrangement.

*Anthers.*—Size — Insignificant. Color — Yellow.

*Filaments.*—Length — Insignificant. Color — Yellow.

*Pollen.*—Color — Yellow.

Pistils:

*Number.*—One for each floret.

*Styles.*—Length — Insignificant. Color — Insignificant.

Stigmas: Color — Insignificant.

Characteristics of ovaries: Inferior bicarpellate.

The distinctive and advantageous characteristics of this chrysanthemum cultivar reside mainly in its vigorous growth habit with production of large, golden bronze, semi-incurve standard blooms carried on a strong, long stem. This cultivar is further distinguished in that it may be flowered the year round in high light areas with a uniform eight-week response under high and low temperatures. The eight-week response of this cultivar make it one week earlier than either "Onward" (U.S. Plant Pat. No. 3,194) or "Topaz" (U.S. Plant Pat. No. 4,252).

I claim:

1. A new and distinct variety of chrysanthemum plant, substantially as herein shown and described, characterized by the unique golden bronze coloring of its very large blooms, its uniform eight-week response, its strong and upright growth habit, and its capability of being flowered at any time during the year.

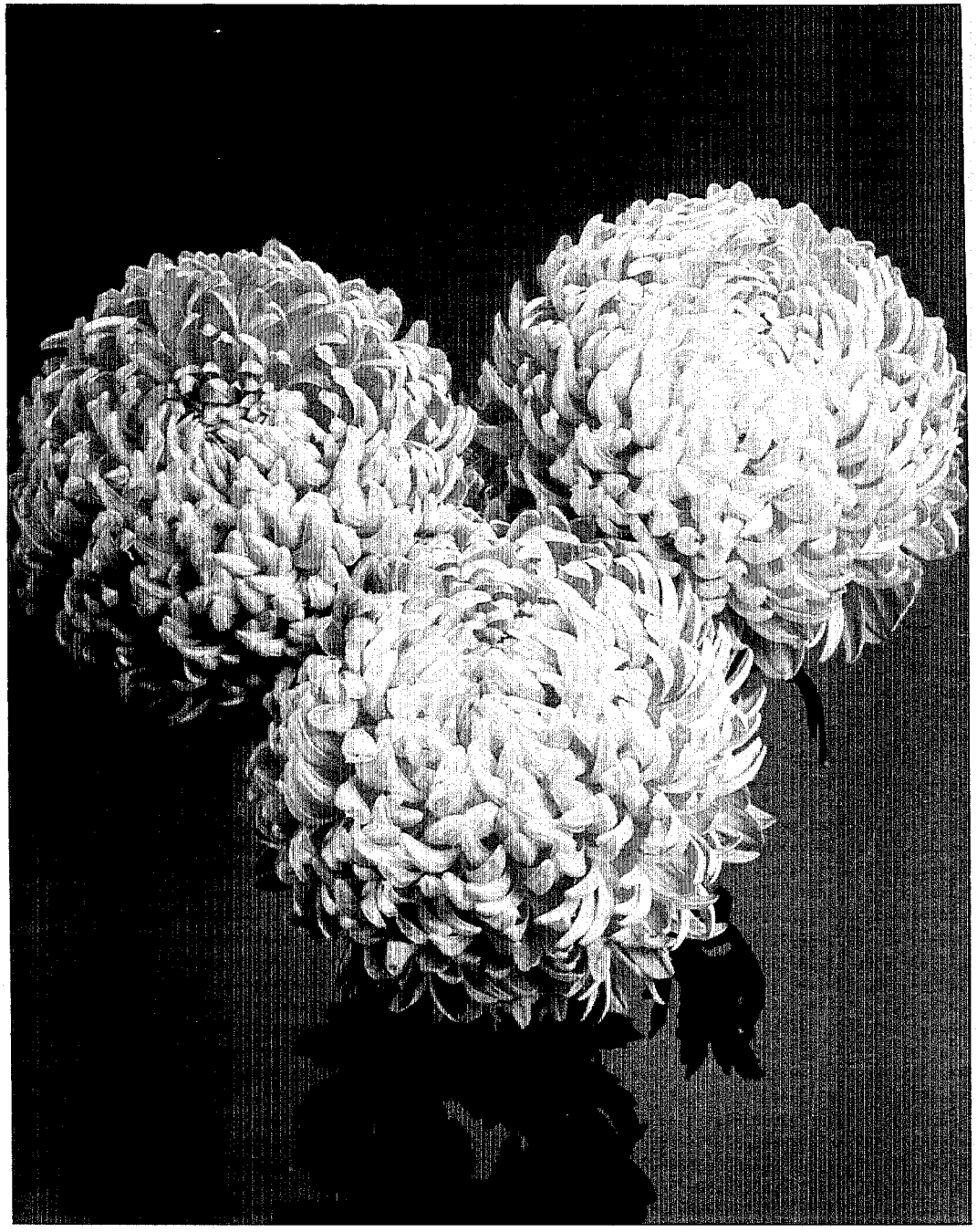

* * * * *